(12) United States Patent
Stähler et al.

(10) Patent No.: US 7,361,314 B1
(45) Date of Patent: Apr. 22, 2008

(54) MICROFLUID REACTION CARRIER HAVING THREE FLOW LEVELS AND A TRANSPARENT PROTECTIVE LAYER

(75) Inventors: Cord Fredrich Stähler, Weinheim (DE); Manfred Müller, München (DE); Peer Friedrich Stähler, Mannheim (DE); Ralf Mauritz, Frankfurt (DE)

(73) Assignee: febit biotech GmbH, Heidelberg (DE)

( * ) Notice: Subject to any disclaimer, the term of this patent is extended or adjusted under 35 U.S.C. 154(b) by 929 days.

(21) Appl. No.: 10/030,182

(22) PCT Filed: Aug. 1, 2000

(86) PCT No.: PCT/EP00/07445

§ 371 (c)(1),
(2), (4) Date: Mar. 28, 2002

(87) PCT Pub. No.: WO01/08799

PCT Pub. Date: Feb. 8, 2001

(30) Foreign Application Priority Data

Sep. 1, 1999 (DE) .................................. 199 35 433

(51) Int. Cl.
*B01L 3/00* (2006.01)
(52) U.S. Cl. ..................... 422/102; 422/68.1; 422/100; 422/130; 436/166; 436/172; 436/174; 436/180
(58) Field of Classification Search ............... 422/68.1, 422/82.05, 82.06, 82.08, 82.09, 99, 100, 422/102, 179, 130; 436/164, 165, 166, 172, 436/174, 175, 180
See application file for complete search history.

(56) References Cited

U.S. PATENT DOCUMENTS

| | | | |
|---|---|---|---|
| 3,979,637 A * | 9/1976 | Siegmund ................... 315/12.1 |
| 5,534,328 A | 7/1996 | Ashmead et al. |
| 5,595,712 A | 1/1997 | Harbster et al. |
| 5,846,708 A * | 12/1998 | Hollis et al. .................... 435/6 |
| 5,858,195 A | 1/1999 | Ramsey |
| 5,863,502 A * | 1/1999 | Southgate et al. ............ 422/58 |
| 5,867,266 A | 2/1999 | Craighead |
| 5,872,010 A | 2/1999 | Karger et al. |
| 5,872,623 A * | 2/1999 | Stabile et al. ................. 356/73 |
| 6,143,248 A * | 11/2000 | Kellogg et al. ............... 422/72 |
| 6,191,852 B1 * | 2/2001 | Paffhausen et al. ......... 356/244 |
| 6,210,910 B1 * | 4/2001 | Walt et al. ................. 435/7.32 |
| 6,485,690 B1 * | 11/2002 | Pfost et al. ................. 422/102 |

FOREIGN PATENT DOCUMENTS

| WO | WO 93 22053 | 11/1993 |
|---|---|---|
| WO | WO 96/15450 | 5/1996 |
| WO | WO 98/00231 | 1/1998 |
| WO | WO 98/02728 | 1/1998 |
| WO | WO 99/41015 | 1/1999 |
| WO | WO 99 14368 | 3/1999 |
| WO | WO 99 46045 | 9/1999 |

* cited by examiner

*Primary Examiner*—Jill Warden
*Assistant Examiner*—Dwayne K. Handy
(74) *Attorney, Agent, or Firm*—Rothwell, Figg, Ernst & Manbeck

(57) ABSTRACT

The present invention relates to a microfluid reaction carrier intended for the purely fluid or light-controlled synthesis or analysis of oligomers or polymers. The reaction carrier comprises a structure of flow channels for the fluids, while supply channels and discharge channels parallel to the latter form an angle relative to the plane of the structure of the flow channels (reaction areas).

29 Claims, 19 Drawing Sheets

Figure 6:
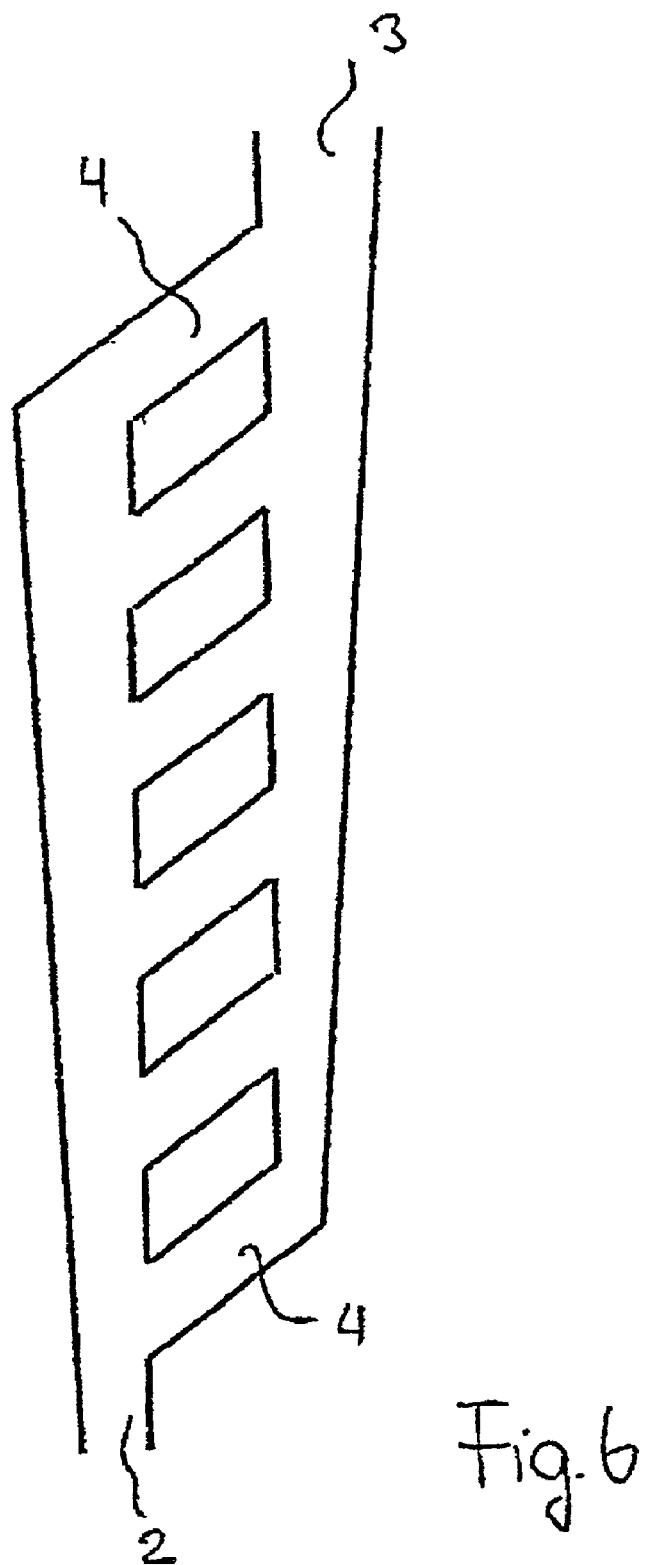

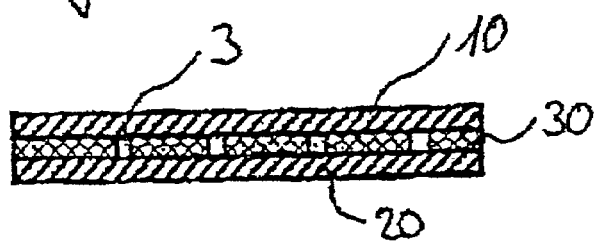
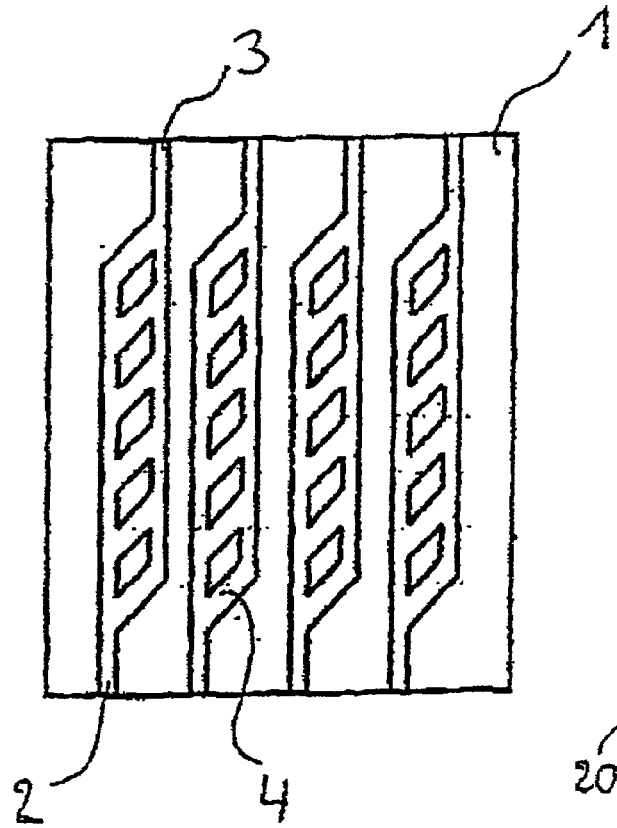

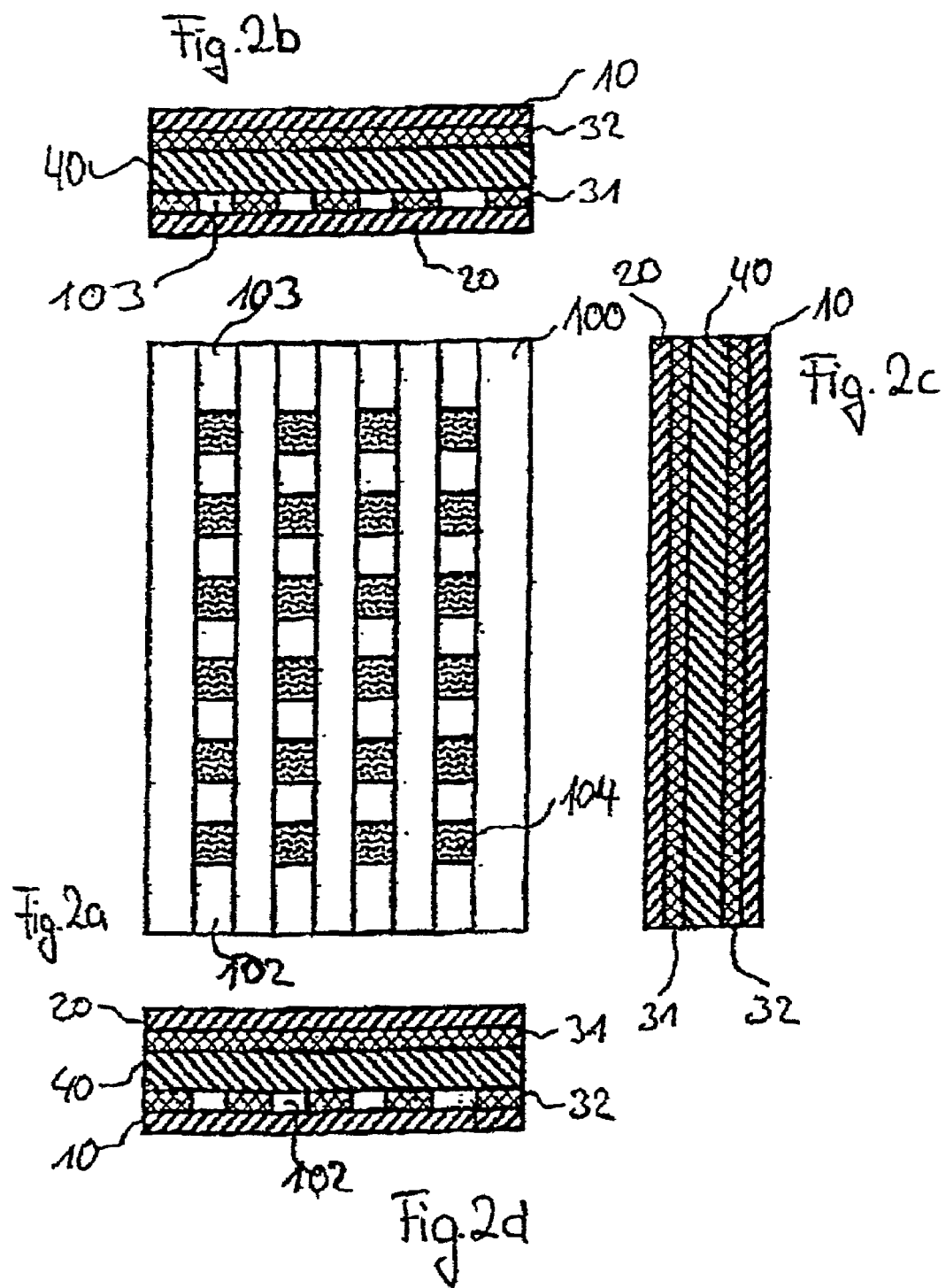

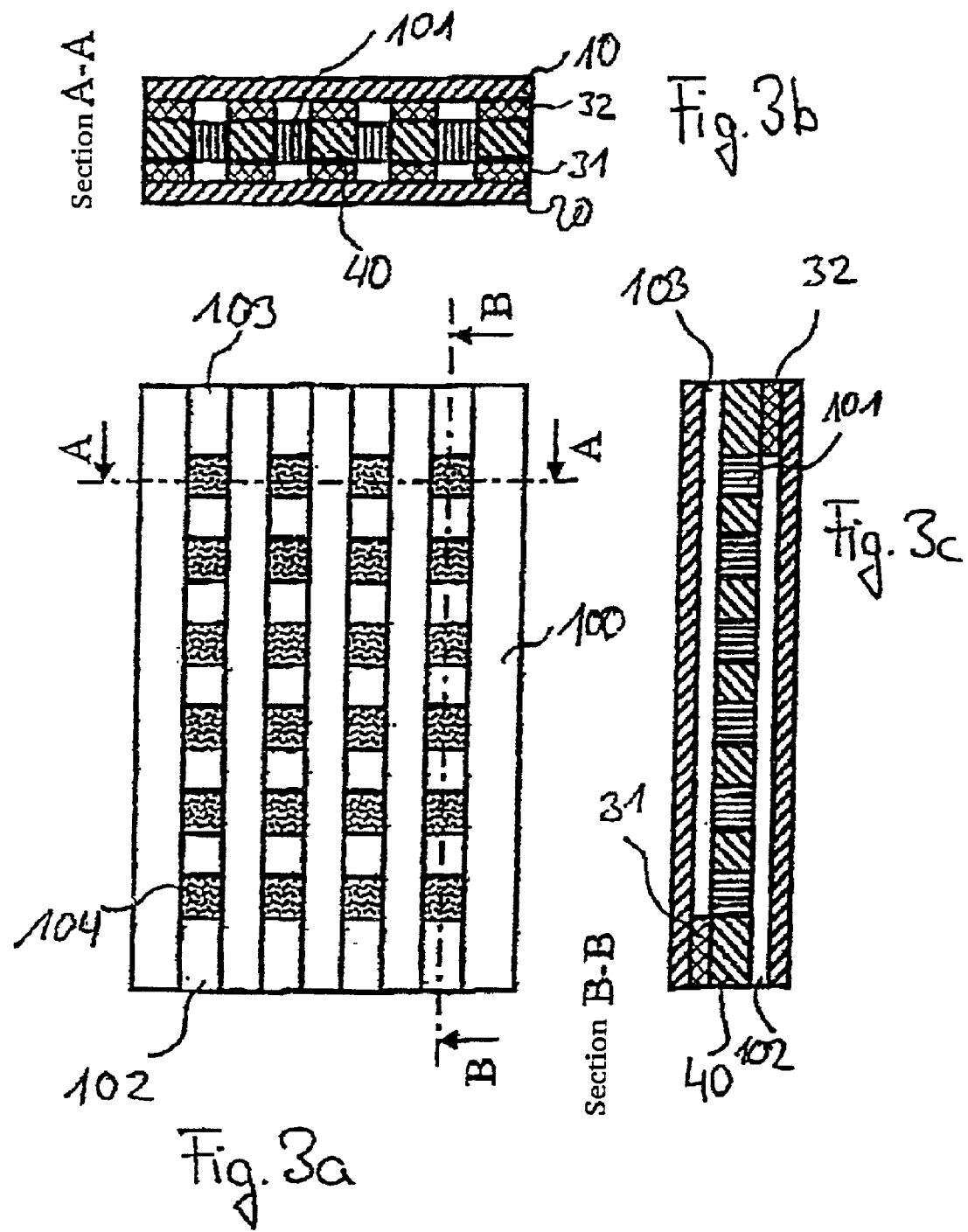

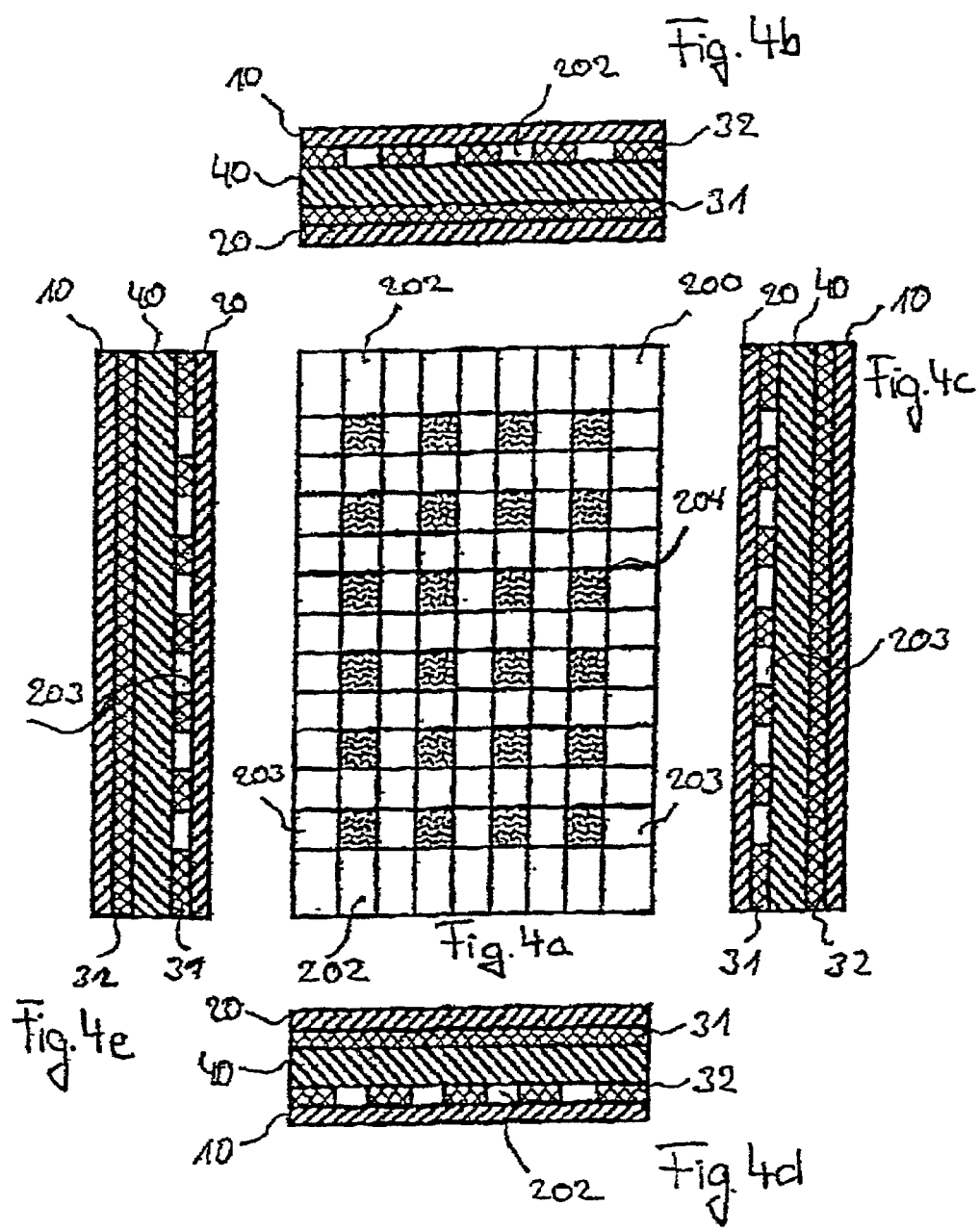

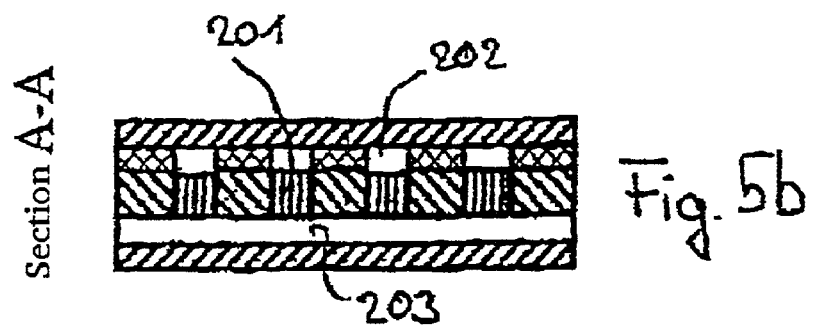
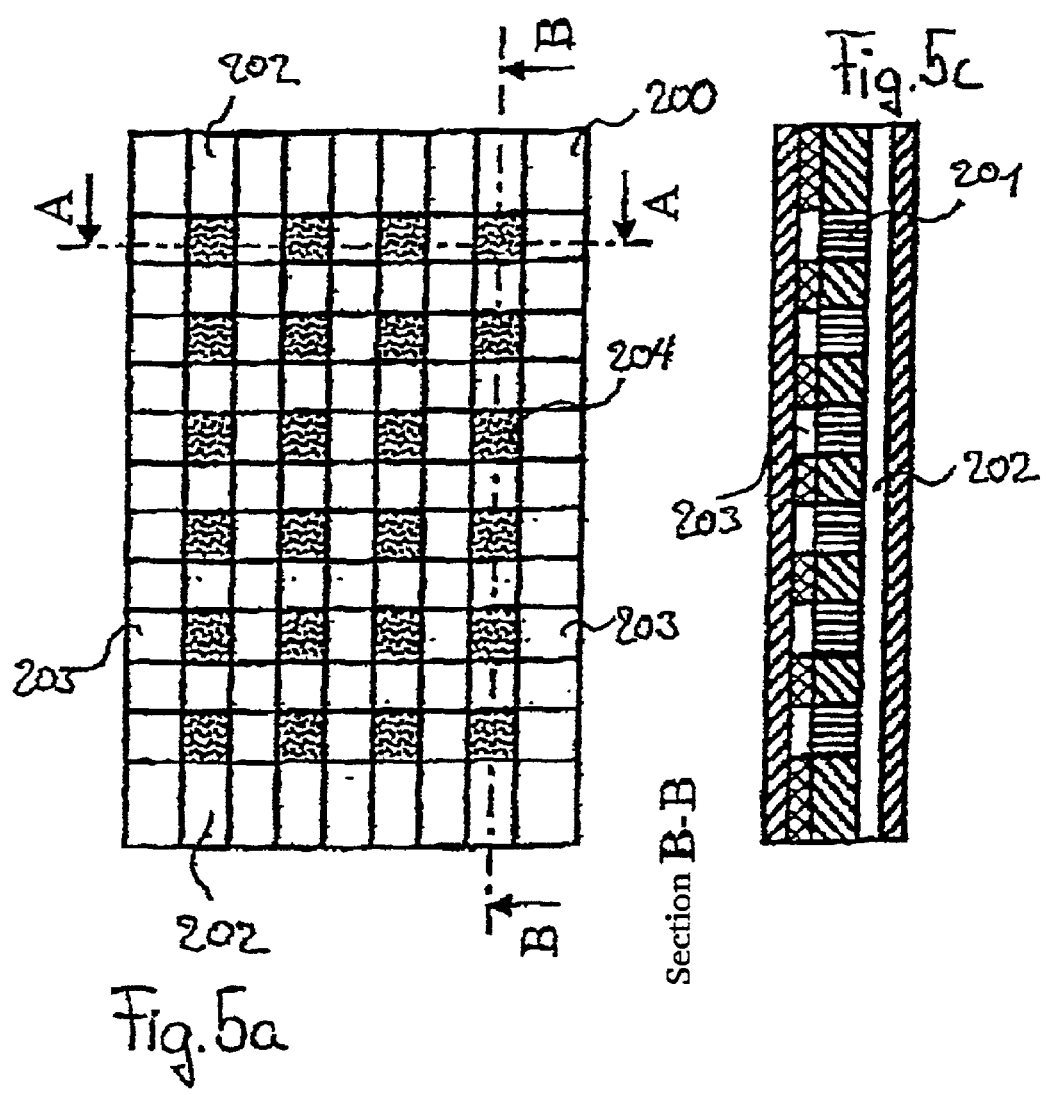

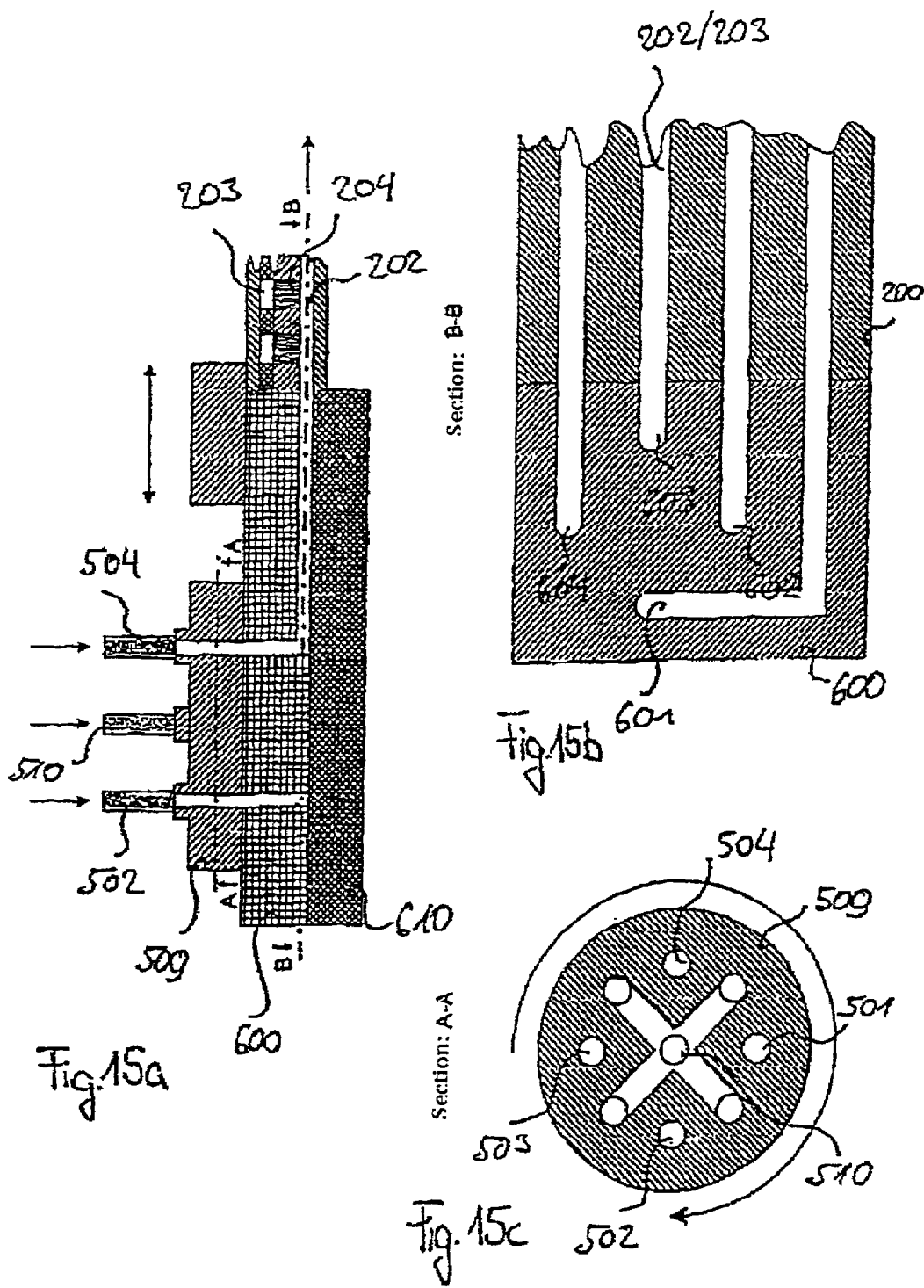

MICROFLUID REACTION CARRIER HAVING THREE FLOW LEVELS AND A TRANSPARENT PROTECTIVE LAYER

CROSS-REFERENCE TO RELATED APPLICATION

This application is a National Stage entry of International Application No. PCT/EP00/07445, filed Aug. 1, 2000, the entire specification claims and drawings of which are incorporated herewith by reference.

The present invention relates to a microfluidic reaction support which, depending on the embodiment, makes possible a purely fluidic or else light-controlled synthesis and analysis of oligomers or polymers. In addition, any other application as miniaturized chemical or biochemical synthesis and analysis platform, for example for application in combinatorial chemistry, is in principle conceivable.

In general, the development of microfluidic systems is still in its infancy. However, even now they represent an important field, for example, in the area of micropumps or microvalves. The focus of present studies in this field is on the preparation of miniaturized structures, preferably using semiconductor technology methods.

Micrometering systems link microminiaturized pumps and valves to sensors for drive and regulator circuits.

Such systems are currently developed and tested for specific applications, for example for dosing of medicaments or metering of very small amounts of liquids in a free jet according to the inkjet printer principle. These are used, for example, for preparing "polymeric probe arrays" by spraying various biochemical substances on defined positions of a support body.

The mixing of media in microfluidic systems, for example in chemical microreactors or in bioreactors but also in chemical analysis systems, has not been extensively studied to date. If very rapid mixing is required, however, the use of specifically constructed vortex zones or the use of a likewise miniaturized mixer can achieve very high mixing rates. The development of micromixers is not market-ready yet and is for the most part still in the experimental stage. The interaction of fluid and wall, which is important for the microfluidic reaction support of the invention, has not to date been studied in detail.

Complete microfluid analysis systems have been realized previously only in some cases, for example in systems for analyzing the heavy metal content of ground water. Test samples and functional samples of such microfluid analysis systems are prepared by using preferably various established silicon technologies such as, for example, isotropic and anisotropic etching.

A great disadvantage of silicon technology is the relatively high cost of material. For this reason, various inexpensive technologies are currently developed, which allow preparation of microstructures as "throw-away articles". Three of these methods are micro injection molding, miniaturized hot molding and "LIGA" (light-induced galvano-molding) technology. These methods allow in the experimental stage the preparation of microstructures with dimensions of less than 1 μm.

These developments are presently applied, for example, in DNA analysis. The current subject of research here is a very rapid and therefore highly parallel detection. The combination of hybridization as detection principle and optical signal detection is in the most advanced stage. In the USA, enormous resources are being used to advance the development of these miniaturized detection chips. The analytical performance here is in the range from $10^4$ to a maximum of $10^5$ bases per hour.

The aim is therefore to develop a technology with the aid of which it is possible to analyze about and greater than $10^5$ bases per hour and to process the obtained data such that meaningful interaction between user and the device to be used is possible. The core of such a device is the subject of the present invention and is described as microfluidic reaction support below. This reaction support of the invention is intended to form, for example, the central component of systems for automatic fragment synthesis and fragment analysis of oligomers or polymers. A system of this kind is described in the patent application 19924327.1.

The reaction support of the invention includes a structure of microchannels of different size, geometry and function. Part of the microchannels serves to supply and discharge fluid. All other channels serve as reaction areas, and it is also possible, depending on the application, to integrate optionally fluid reservoirs, etc. into the microstructure. The flow through the reaction support is either two-dimensional or three-dimensional. The two-dimensional design variant comprises at least in each case one feed and one discharge channel in a single flow level. These two channels are connected by a plurality of channels which run approximately perpendicular thereto, and these perpendicular connecting channels serve as preferred reaction areas. The thus resulting reaction channels can likewise be divided again into smaller channels, each reaction channel comprising one or more reaction areas. These reaction areas may be arranged, for example, along the channel.

The more complex three-dimensional design variant comprises three flow levels. The feed channels are arranged in each case parallel to one another in a first flow level and the discharge channels are arranged in each case parallel to one another in the third flow level, and feed and discharge channels are arranged in a perpendicular projection either parallel to one another or at an angle to one another, said angle being chosen preferably as approximately 90°. Moreover, perpendicular channels which form a third flow level and connect the feed channels of the first level with the discharge channels of the third level are arranged in the angled arrangement at the crossover points of the channels in their perpendicular projection or in the parallel arrangement along the channels. Said connecting channels are substantially narrower than the feed and discharge channels. This makes it possible for fluid to flow over the reaction areas in the feed and discharge channels without entering the reaction channels. Several reaction channels together form a reaction area.

Thus, the technical preconditions for a very rapid, efficient and thus inexpensive provision of a multiplicity of reaction areas have been created, for example for the integrated synthesis of a multiplicity of polymeric probes and the analysis of a multiplicity of polymer fragments by means of said probes.

In all design variants, the fluids are discharged from the reaction areas, without said fluids coming into contact with another reaction area of the entire reaction support. This is especially relevant in reactions whose waste products could damage or destroy other reaction areas.

All three variants of the microfluidic reaction support of the invention have a cover layer on both the top and the bottom. In the case of the two-dimensional structure and also in the case of the parallel feed and discharge channels of the three-dimensional structure, at least one of the cover layers has a transparent structure in order to make possible a light-controlled photoactivation in the individual reaction areas by individual illumination, for example by means of a programmable light source matrix as described in the patent application 199 07 080.6. All three variants are constructed preferably with two cover layers, in order to make possible a permanent optical process control in the reaction support and measurement of detection reactions in transmitted light.

Various protective groups which are partly used also in the synthesis of microarrays are known and available for light-dependent photoactivation. Examples of protective groups included here are MeNPOC, NPPOC and its derivatives and also some older protective groups which have been described by Pillai (Synthesis, 1980); Hadrisan and Pillai (Proc. Indian nat. Sci. Acad. 53, 1987) or Birr et al (Liebigs Ann. chem. 763, 1972).

Moreover, methods in which photoactivation leads indirectly via light-dependent activation of an acid (photo acid) to a subsequent location-specific removal of an acid-labile protective group such as, for example, DMT are also known (see Gao et al in WO 9941007). A similar mechanism can be utilized if suitable photoresists are applied to the reaction support (see McGall in PNAS 93, pp. 13555-13560, 1996).

In addition to these chemical methods it is also conceivable to control synthesis by photoactivation and photodeactivation of enzymes.

The more complex three-dimensional structure containing the feed and discharge channels rotated at an angle makes it possible to individually rinse each individual reaction area of the vertically arranged microchannels. This is carried out by rinsing in each case one feed channel with fluid and discharging fluid through one discharge channel. The fluid flows through the feed channel into the perpendicular microreaction channels and out of the reaction support again through the discharge channel. In the same way it is possible to rinse a plurality of reaction areas at the same time and even with different fluids. Thus the microfluidic reaction support of the invention, which has a "cruciform structure" due to the angled arrangement, opens up a multiplicity of applications of combinatorial chemistry or DNA analysis.

Another application is suffusing initially all feed and discharge channels alternately with starting materials, with the fluid supply and fluid discharge functions of the feed and discharge channels alternating from cycle to cycle. If, for example, each channel is rinsed with a different building block of a polymeric probe to be synthesized, then it is possible to generate over a few cycles a large variety of oligomeric or polymeric probes in the individual reaction areas of a reaction support, due to the use of the cruciform structure. Additionally, the synthesis of individual probes of any specificity in a single reaction area is possible without problems by individually driving a reaction area as described above. Thus the inventive microfluidic reaction support with cruciform structure provides the possibility of efficient wet-chemical "probe array" synthesis of oligomeric or polymeric probes. This procedure is denoted "fluidic multiplexing" hereinbelow. This also makes possible in-situ synthesis by means of process monitoring and also integrated synthesis and analysis.

The purely fluidic reaction control requires no transparent cover layers which are, however, likewise sensible for optical process control and for recording detection reactions. In this case, detection may be carried out likewise either in transmitted light or else in back light from one side. If the three-dimensional cruciform structure with its feed and discharge channels arranged by rotation at an angle is combined with the light-controlled photoactivation of the reaction areas of microchannels, the efficiency of synthesizing oligomeric or polymeric probes can be increased still further. It is possible to integrate both the light source matrix as light source and the required detector into the microfluidic reaction support. The same can be said for integrating a CCD matrix as second opposite cover layer. It is also possible to connect a programmable light source matrix as cover layer directly. This suggests itself, in particular if the microfluidic reaction support is integrated into a device as a fixed component and is purified, for example chemically, between uses and has only to be changed for maintenance purposes. If the microfluidic reaction support is exchanged after each use, then, however, direct integration is not sensible. In this case, it is recommended rather to arrange the components in the system accordingly.

The invention likewise relates to supplying the microfluidic reaction support with the appropriate fluids. For this purpose a likewise novel integrated valve system was designed. This allows rapid provision of a multiplicity of fluids in the feed and discharge channels of the microstructure.

This fluid supply system has been designed for applying the microfluidic reaction support of the invention to the synthesis of arrays of oligomeric or polymeric probes in the reaction areas. The supply system is similar in the connections and components for the "upper" and "lower" feed and discharge channels. All channels are individually supplied from one side via a multiplex valve described below. All channels are combined at the in each case corresponding other end of the channel, and this combining is used for feed and discharge with uniform rinsing of all reaction areas. When synthesizing oligomeric or polymeric probes in the reaction areas, this refers to all cycles except for feeding the specific individual building blocks consisting of, for example, one or more nucleotides in the case of DNA synthesis. If it is intended to reach all reaction areas and not to select them specifically, then it is better to choose a flow-optimized feed such as, for example, dual ramification, rather than via the multiplex valve, which has a higher risk of delay. However, the valve is required for feeding the specific building blocks. Said valve connects the microchannels of the reaction support on one side with an at most identical number of individual tanks and a group connection on the other side. In one valve position, in each case one tank is connected with one or more channels of the reaction support. If the fluid of a single tank is intended to enter more than one channel or channel bundle of the reaction support in a single cycle, first one channel and then further channels are provided in series. The group connection corresponds to the combination of the channels on the in each case opposite side of the reaction support. It serves to efficiently rinse valve and reaction support.

The connections of the microfluidic reaction support to its fluid supply and fluid disposal are an important element. If the reaction support is purified time and again and reused in the specific application, a complicated connection technique, for example to the multiplex valve, may be provided for. In this case, in particular in the case of a large number of channels, a design with a multiplicity of very small channels in "legs", in analogy to semiconductor processor technology, is possible. The disadvantage of this design with respect to flow is the risk of deposits in the bends and kinks of the individual microchannels. Here, subsequent rinsing may be provided for, as for avoiding delays. For the application variant in which the reaction support is exchanged after each application, rapid connections which seal without adhesive are required. In this connection, it is possible, for example, to connect flat to the front of the reaction support, with a through bend-free channel course. Thus the risk of delay is minimal. A second alternative is pressing the bottom of the reaction support onto the fluid feed. In this connection, suitable seals resistant to chemicals have to be provided for in each case.

In one aspect of the invention, purification means in particular a complete regeneration of the reaction support. Said support can then be used again in the regenerated state for a new polymer synthesis. In the case of chemical purification, it must preferably be taken care that the linkage site required for attaching a first polymer building block is not destroyed. The predetermined breaking point necessary for chemical purification may be cleaved by chemical (e.g. wet-chemical, photo-chemical, electrochemical) or biological (e.g. enzymic) transformation. Preference is given to providing the predetermined breaking point during the first surface derivatization of the microfluidic reaction support, preferably in the linker system which connects the surface to the first polymer building block. In each case it is guaranteed that the predetermined breaking point cannot be broken by the analyte or reagents used during synthesis or during analysis.

One-Stage Process:

The predetermined breaking point is broken by a single transformation. Examples of this are base-labile linkers, acid-labile linkers, oxidation-labile linkers or degradation with the aid of suitable enzymes.

Apart from chemical purification, it is thus also possible to carry out an enzymic purification of the reaction support. In this case, the polymeric or oligomeric probes linked to the reaction support are cleaved or "digested" with a DNA- or RNA-degrading enzyme or a peptide-cleaving enzyme, resulting in degradation of a part or all of the probes. Afterward, the reaction support can be used again for synthesizing new probes.

Suitable enzymes are nucleases such as exonucleases or endonucleases which attack one nucleic acid strand from the ends or within the probe strand and which leave behind nucleotides or nucleosides as cleavage products. In the case of RNA, it is possible to use RNAses (RNAse H, etc.) which, if an RNA-DNA double strand has been generated, selectively cut the RNA part resulting in cleavage of the entire probe in the case of RNA probes and of the RNA section in the case of RNA part sections as predetermined breaking point. Likewise, a reaction support can be regenerated with DNA probes by using DNAses (DNAse I, DNAse II, etc.), and, as a result, both single-stranded and double-stranded DNA can be degraded.

Likewise, it is possible to use peptide-cleaving enzymes for degradation of peptide probes or peptide sequence sections as predetermined breaking point.

Multistage Process:

The predetermined breaking point is broken in a multistage process, i.e. the predetermined breaking point is masked in some form. This requires firstly removing said masking in one or more steps before in the subsequent step the predetermined breaking point can then finally be broken.

As an example a masked photolabile linker can be used, in which an o-nitro function required for photolability is only generated by a preceding transformation. This may take place, for example, by oxidation of an amino function. This, not necessarily specific, oxidation step may be carried out enzymatically or wet-chemically. Once the o-nitro function has been generated, it is then possible for the predetermined breaking point to be cleaved by irradiation with light.

Another possible solution is to generate in a first step a double-stranded DNA sequence by adding an analyte complementary to the linker, which is then in the next step recognized by a specific enzyme (restriction enzyme) and is removed by specific cleavage.

When using an RNA part section as probe "base", it is possible to chemically regenerate the reaction support likewise in several stages. In this connection, the synthesis is initially carried out using 2'-OH-protected phosphitamide building blocks. After hybridization and analysis, the protective group is regenerated by cleaving off the RNA part section, resulting in a free 2'-OH group. This may be followed in a subsequent chemical reaction step by cleavage of the ribose sugar with the aid of periodate or other oxidants and removal of the probe from the reaction support by β elimination.

The above-described purification (receptor removal) processes have independent significance within the scope of the invention, irrespective of a specific embodiment of the support. The applicant reserves putting forward, where appropriate, independent patent claims regarding the described technology of purification or receptor removal.

It should be pointed out that it is also possible to remove the receptor or molecule by cleavage in the sense explained above, in order to collect molecules removed by cleavage and to use said molecules for further chemical processes, for example for a synthesis step. In this sense, the purification processes may be seen as steps for obtaining molecules synthesized on a support.

The microfluidic reaction support of the invention is constructed in several layers, as is common also in semiconductor microtechnology. In this case it is possible to distinguish between dividing the microstructure into functional layers and into layers due to the construction.

While a two-dimensional structure has at least three functional layers, a three-dimensional structure consists of at least five functional layers. These functional layers are described in more detail below. During production is it often possible to integrate a plurality of these functional layers by means of suitable production methods into a layer due to the construction.

The functional layers of the two-dimensional structure contain a central structural layer into which the microflow structure of channels, reaction areas and reservoirs is introduced. It is connected with an upper and a lower cover layer and may be made of glass, plastic or silicon. Depending on the design, the material used may be transparent or else lightproof. An example of lightproof material, which is recommended, is Futoran glass from Schott, silicon or Teflon.

The three-dimensional structures consist of five functional layers, a first, "upper" cover layer, a structure of microchannels, located underneath said cover layer, for feeding and discharging fluid in a manner analogous to the two-dimensional structure, a central level of perpendicular, smaller (preferably by at least a factor of 10) microchannels which serve as reaction areas. At the "bottom" a level for fluid supply and a cover layer follow, both of which are designed similarly to the "top". Overall, the reaction support is a construction mirrored at a central plane. The preparation need not necessarily follow the functional layers. Thus it is possible to integrate the feed and discharge structure both into the central layer and into the cover layer. It is possible to use for the central layer with the perpendicular microchannels as reaction areas, for example, suitable silicon wafers from the semiconductor technology, which has etched "pores", from Siemens or fused glass fibers (glass fiber wafers) from Schott, having etched-out cores and a size ratio between wall thickness and channel diameter of preferably 1 to 5. In order to improve precise rinsing of only the "driven" reaction channels, it is possible to supplement the central functional level with an upper and a lower intermediate layer. Said layer prevents or makes more difficult unwanted streaming-in of fluids (hydrophilic or hydrophobic barriers).

The preparation methods required can be distinguished according to the material used. In the case of silicon wafers, glass wafers and glass fiber wafers (with and without core), the connection techniques used are bonding methods. The parts such as, for example, the various wafers are prepared by etching techniques and also sawing and polishing. When plastics such as Teflon which is lightproof and COC or polystyrene which is transparent are used, methods such as injection molding, hot molding or LIGA are used. The components are connected, for example, by means of adhesive bonding or ultrasound welding or by mechanical pressure sealing by means of a holder or a frame.

The upper cover layer seals on the outside the microflow structure lying underneath. This produces the microchannels. The layer is transparent for introducing light into said channels. In order to optimize the optics, it is also possible to use microlenses made of glass from Mikroglas or plastic (IMM Mainz). Likewise possible is the use of a honeycomb structure made of fused glass fibers which was developed, for example, by Schott or ITT and is used, for example, in night vision equipment. To this end, long glass fiber bundles are heated such that they fuze and [illegible]. These may then be bonded to glass or silicon or bonded or welded to plastics.

The proper use of the microfluidic reaction support of the invention is as follows: firstly a group of reaction areas is addressed via the microchannels of a two- or three-dimensional microstructure. After the reaction has taken place there, the reaction products forming in the individual reaction areas are discharged through microchannels, without the reaction product flowing through another reaction area. In this connection, driving of the reaction areas in the described three-dimensional cruciform structure may be utilized for purely fluidic synthesis of oligomers or polymers from monomers, oligomers or polymers or else for accelerating the light-controlled synthesis or a combined wet-chemical and light-controlled synthesis of oligomers or polymers by the described intelligent multiplexing of the starting materials.

In the meantime, all reaction areas and microchannels are optically controlled through transparent cover layers, this being a platform for an in-situ synthesis, a permanent process control and regulation of the processes in the microstructure. This creates the basis for a comprehensive quality assurance. Light signals of detection reactions, which are produced in the reaction areas by chemical (e.g. luminescence), biochemical (e.g. bioluminescence) or light-induced (e.g. fluorescence) reactions, can be recorded in an integrated apparatus for synthesis and analysis, which encloses the fluidic microprocessor and is described in the patent application 19924327.1. Furthermore, absorption can be measured in the reaction support by recording light signals which pass through the microchannels and reaction areas in a transmitted-light process or are reflected in a backlight process. This may be utilized, for example, for an extended qualitative quality assurance.

This microfluidic reaction support of the invention has many different advantages: first, the reaction products are discharged from each reaction area without another reaction area coming into contact with the reaction products. This makes it possible to carry out reactions for synthesis and analysis in those reaction areas which generate reaction products (final products or intermediates) which would be harmful to other reaction areas.

Compared with planar surfaces, the three-dimensional microchannels have a larger surface area which can be utilized as a solid phase.

The use of microstructures reduces the amount of fluid required for the reactions and at the same time increases the reaction rate. This is the case both for covalent bonds and, for example, for the hybridization times for applications in DNA, RNA, PNA, LNA analysis or for protein applications.

Transparent cover layers make possible photoreactions, for example for the light-controlled synthesis of DNA, RNA, PNA, LNA or proteins, etc.

Moreover, the transparent cover layers make possible a permanent process control for regulating the reactions and also the fluidics in the reaction support. This leads to a distinct reduction in the mistakes both in production and in detection, thus increasing the number of analyzable measurements per use of material and time.

A suitable layout of the geometry of the individual reaction areas and the microchannels between the reaction areas makes it possible to specifically influence the beam paths, taking into account the refraction indices present in the reaction support.

The fluidic microprocessors of the invention may be designed as simple components for single use. In principle inexpensive plastic structures are to be preferred here but possible designs are also glass and silicon [lacuna] or else combinations of materials.

Rapid and inexpensive production makes possible a large variety of individual applications in which probe arrays can be synthesized and analyzed specifically, for example by taking into account sequence and gene databases on the Internet.

The reactions always take place on the walls of the microreaction channels. Consequently, the reaction areas always have a three-dimensional structure and have a considerably larger surface area than the planar base area. This three-dimensional geometry thus greatly enlarges the utilizable reaction surface area. Said size of the surface area is very important for the use as solid phase. Said size may be important, for example, for accumulation of oligonucleotides during synthesis in the reaction support as well as for accumulation of sample fragments flowing past during an analysis in the reaction support.

The three-dimensional cruciform structure makes applications, for example, in oligonucleotide analysis or in combinatorial chemistry, etc. possible. Using the two intersecting structures makes it possible to generate quickly a multiplicity of different combinations of oligomers or polymers in the individual reaction areas of the reaction support. This makes possible a very efficient wet-chemical synthesis of an oligomeric or polymeric probe array in a reaction support. This may be controlled by a computer, making it possible to generate any nucleotide combinations in each reaction area. The analysis may likewise be carried out directly in the reaction support, making permanent process control possible.

An appropriate multiplexing of the fluids can reduce the number of preparation cycles of "probe arrays". The location-specific generation of a multiplicity of different oligomeric or polymeric probes of, for example, 20 bases in length on a planar surface by means of local photoactivation requires on each level four synthesis cycles, due to the four different bases. Thus a total number of 4×20=80 cycles is required. There is no systematic possibility of reducing the number of synthesis cycles. On the other hand, synthesis in the microfluidic reaction support offers the possibility of distributing the starting materials, i.e. monomers or oligomers, simultaneously on microfluidic subareas. As a result, it is possible to reduce the synthesis cycles, for example when using tetramers, to a minimum of 5 cycles. The exact number of cycles required for a specific probe array is specific for each probe pattern and can be stated only as statistical average, if the number of reaction areas in the reaction support, the number of parallel fluidic subspaces and the length of the oligomers to be synthesized are given.

The following methods become applicable during the reaction support of the invention: apart from the synthesis of oligomers and polymers up to whole genes and genomes, there is the possibility of "de novo" sequencing of unknown polymers such as DNA, RNA, PNA, LNA, proteins and others via sequence comparison with processed sample material. In addition, it is possible to "re"-sequence polymers, i.e. to compare known with unknown sequences, the known sequences being specifically selected. Likewise, it is possible to prepare substance libraries for screening methods and analytical methods, in particular for nucleic acid analysis via hybridization.

All processes from synthesis to analysis of simple or complex molecules can be integrated in the microfluidic reaction support of the invention and can be carried out very efficiently. This makes possible, for example, the flexible and cost-saving analysis of a large number of polymers by providing a multiplicity of individual and specific polymeric probes in a miniaturized format and subsequent comparison of the probes with analytes of the sample material. This makes it possible to generate in screening methods and analytical methods a large number of measurement data and thus to deal with the wealth of information of biological systems efficiently and in its entirety in a very short time.

Fields of application are also methods and devices for the continuous, discrete fragment analysis, which are accelerated by the present invention and therefore made efficiently usable, and, in principle, all applications of oligomer/polymer analysis, as in liquid chromatography/high pressure liquid chromatography, gas chromatography, thin layer chromatography, gel electrophoresis, capillary electrophoresis, mass spectrometry, etc. and also all "probe array" applications. Furthermore supported is thus substance development and testing of appropriate substances, inter alia in pharmaceutical research. Further important fields of application are molecular diagnostics, DNA and/or RNA analysis, screening for molecular interactions, for example in immunology, molecular biology, histology and combinatorial chemistry.

There is a multiplicity of design variants in the design as well as in the production of the reaction supports, which are depicted in the following drawings:

FIG. 1a shows a two-dimensional structure of the microfluidic reaction support in plan view.

FIGS. 1b and 1c show the corresponding sectional illustrations: the microchannel structure 1 is located in the central flow level 30 of the reaction support. Said central flow level is sealed by the lower cover layer 10 and the upper cover layer 20. The flow structure consists of feed channels 2 and discharge channels 3 and also of the reaction channels 4 located in between and having in each case at least one reaction area.

FIG. 2a shows a three-dimensional structure of the microfluidic reaction support in plan view. FIGS. 2b, 2c and 2d show the corresponding sectional illustrations: the microchannel structure 100 consists of the lower fluid feed structure 32 with microchannels 102 and the upper discharge channel structure 31 with the microchannels 103. In the central layer 40 in between are the connecting or reaction channels in the reaction areas 104, which are arranged nearly perpendicular to the feed and discharge. The cover layers 20 and 30 are optionally transparent or lightproof.

FIGS. 3a, 3b and 3c show again the illustrations of FIGS. 2a, 2b and 2c. In this case, the sectional illustrations illustrate the course of the flow through the feed channels 102, the reaction channels 101 in the reaction areas 104 and through the fluid discharge 103.

FIG. 4a shows a three-dimensional cruciform structure of the microfluidic reaction support in plan view. FIGS. 4b, 4c, 4d and 4e show the corresponding sectional illustrations: the microchannel structure 200 is located in the lower fluid feed and fluid discharge structure 32 with microchannels 202 and the upper fluid feed and fluid discharge structure 31 with the microchannels 203, in each case rotated by 90° toward one another. In the central layer 40 in between are located the connecting or reaction channels in the reaction areas 204, which are arranged perpendicular to the feed and discharge. The cover layers 20 and 30 are optionally transparent or lightproof.

FIGS. 5a, 5b and 5c show once more the illustrations of FIGS. 4a, 4b and 4c. In this connection, the sectional illustrations of the microstructure 200 illustrate the course of flow through the feed and discharge channels 202 and 203 and also through the reaction channels 201 in the reaction areas 204.

FIG. 6 shows the illustration of a single two-dimensional flow structure in analogy to FIG. 1 with altered cross sections of the feed channels 2 and the discharge channels 3 to specifically influence the flow. The cross section of the reaction channels 4 having in each case at least one reaction area is unaltered but may also be modified.

Figure 7:
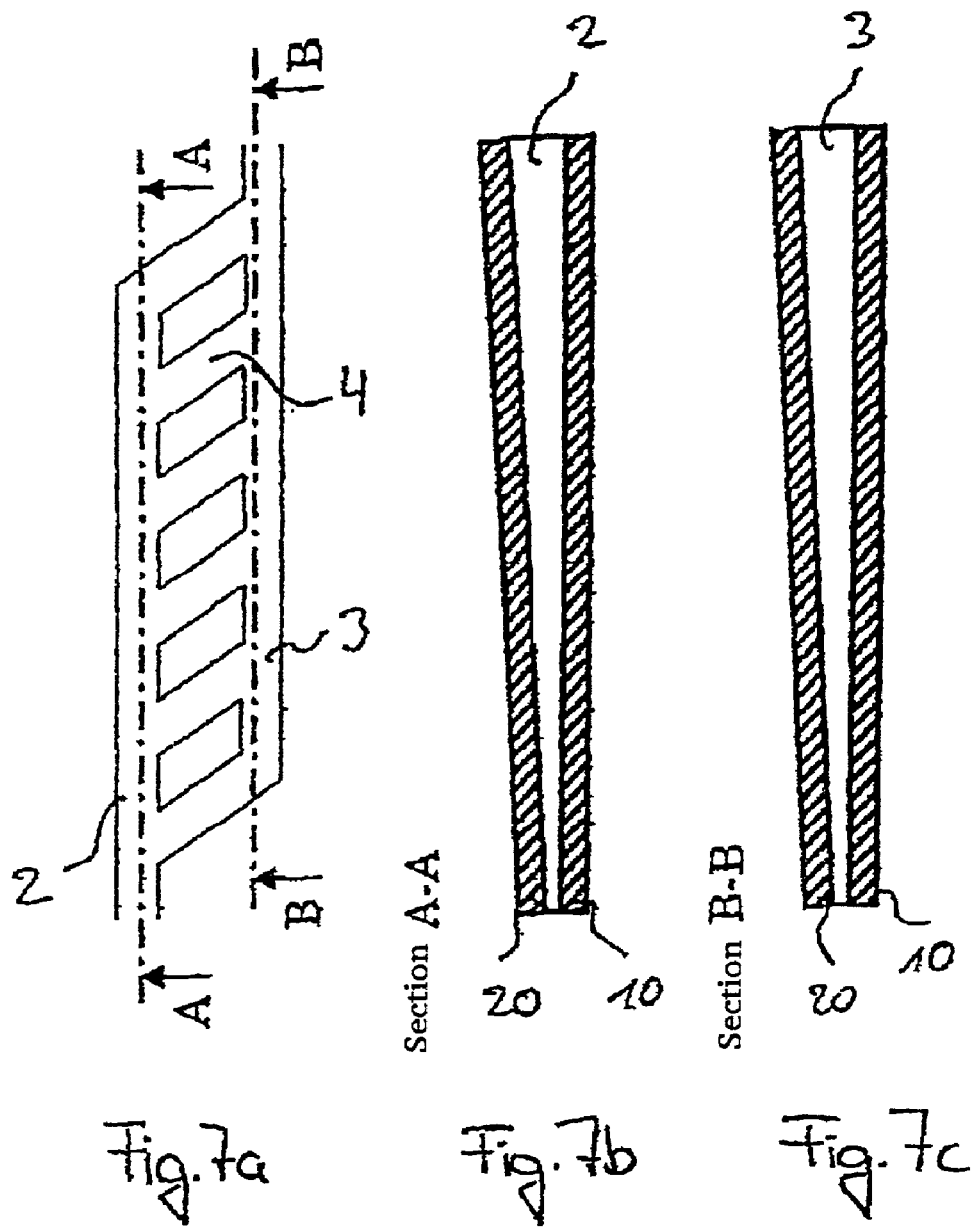

FIG. 7a shows in analogy to FIG. 6 a single two-dimensional flow structure in which the cross sections (shown in FIGS. 7b and 7c) of the feed channels 2 (FIG. 7b) and the discharge channels 3 (FIG. 7c) have been altered at the level of the channels to specifically influence the flow. Here, the cross section of the reaction channels 4 having in each case at least one reaction area has likewise been altered and their size is not uniform. The structure is closed by the cover layers 10 and 20 which are arranged at an angle.

Figure 8:
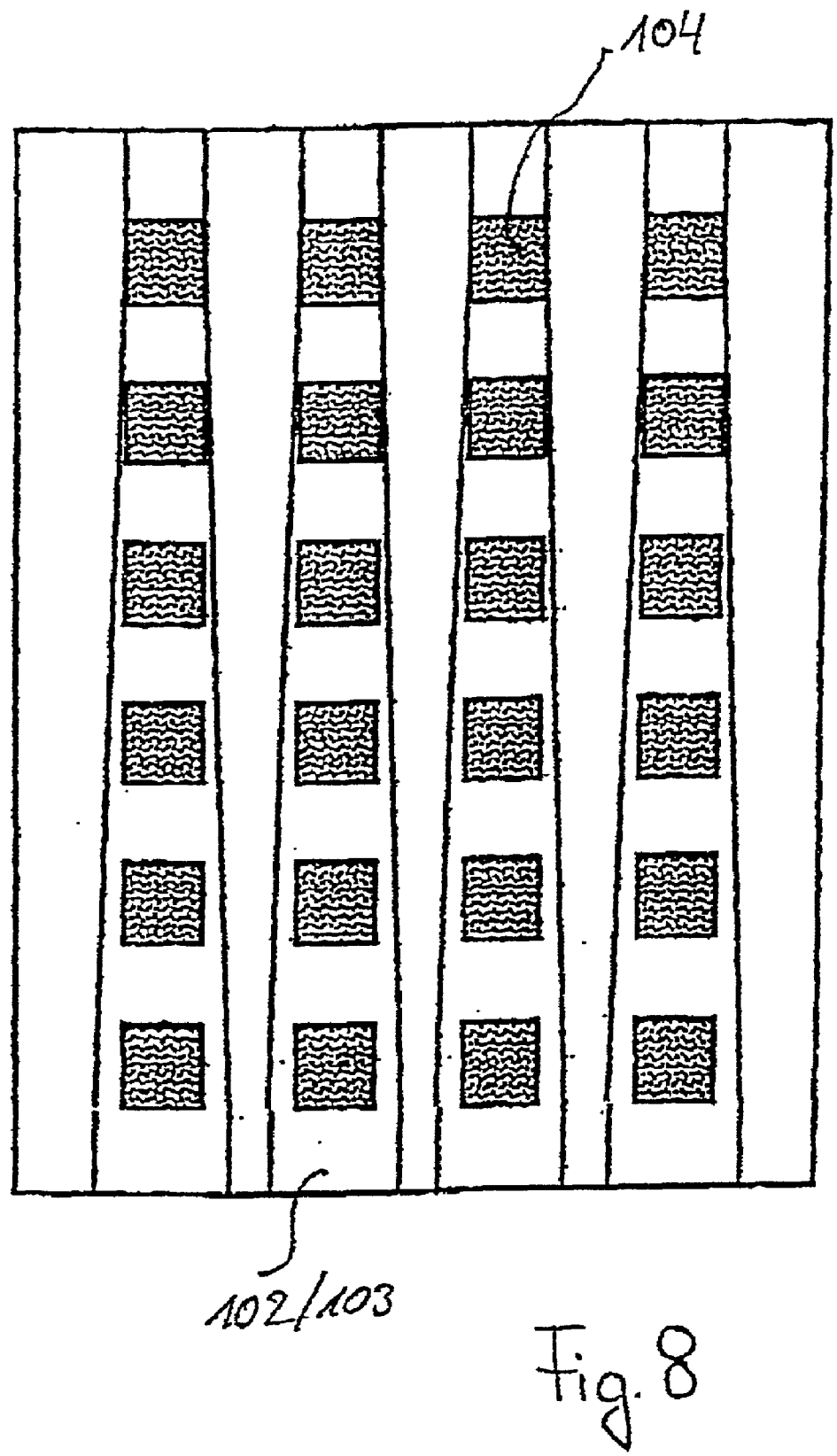

FIG. 8 shows the illustration of a three-dimensional flow structure in analogy to FIGS. 2a—2d and 3a—3c with altered cross sections of the feed channels 102 and the discharge channels 103 to specifically influence the flow. The size of the reaction channels in the reaction areas 104 is unchanged here.

Figure 9:
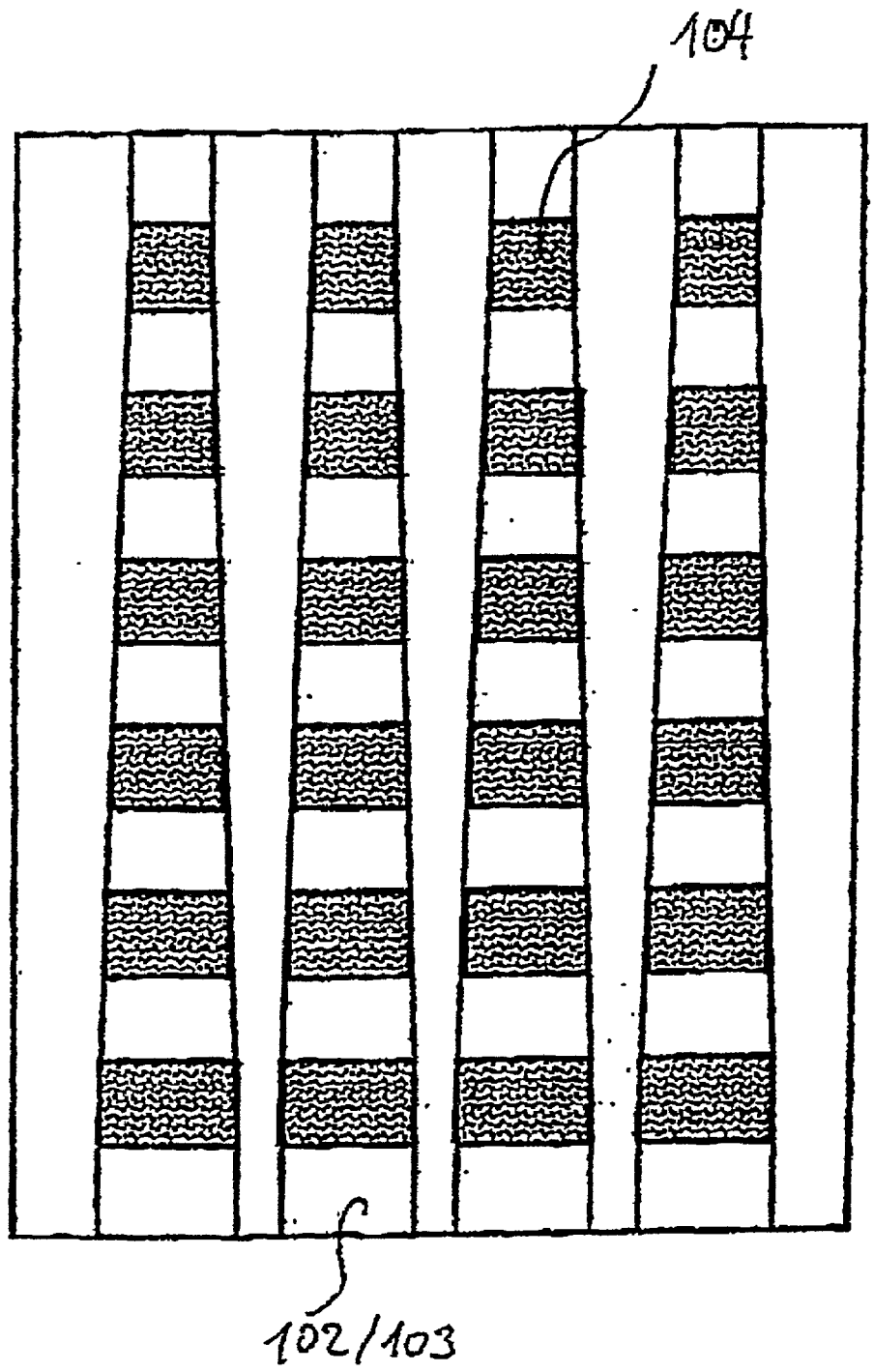

FIG. 9 shows an illustration analogous to FIG. 8, with the size of the reaction areas 104 differing from the size of the feed channels 102 and discharge channels 103.

Figure 10:
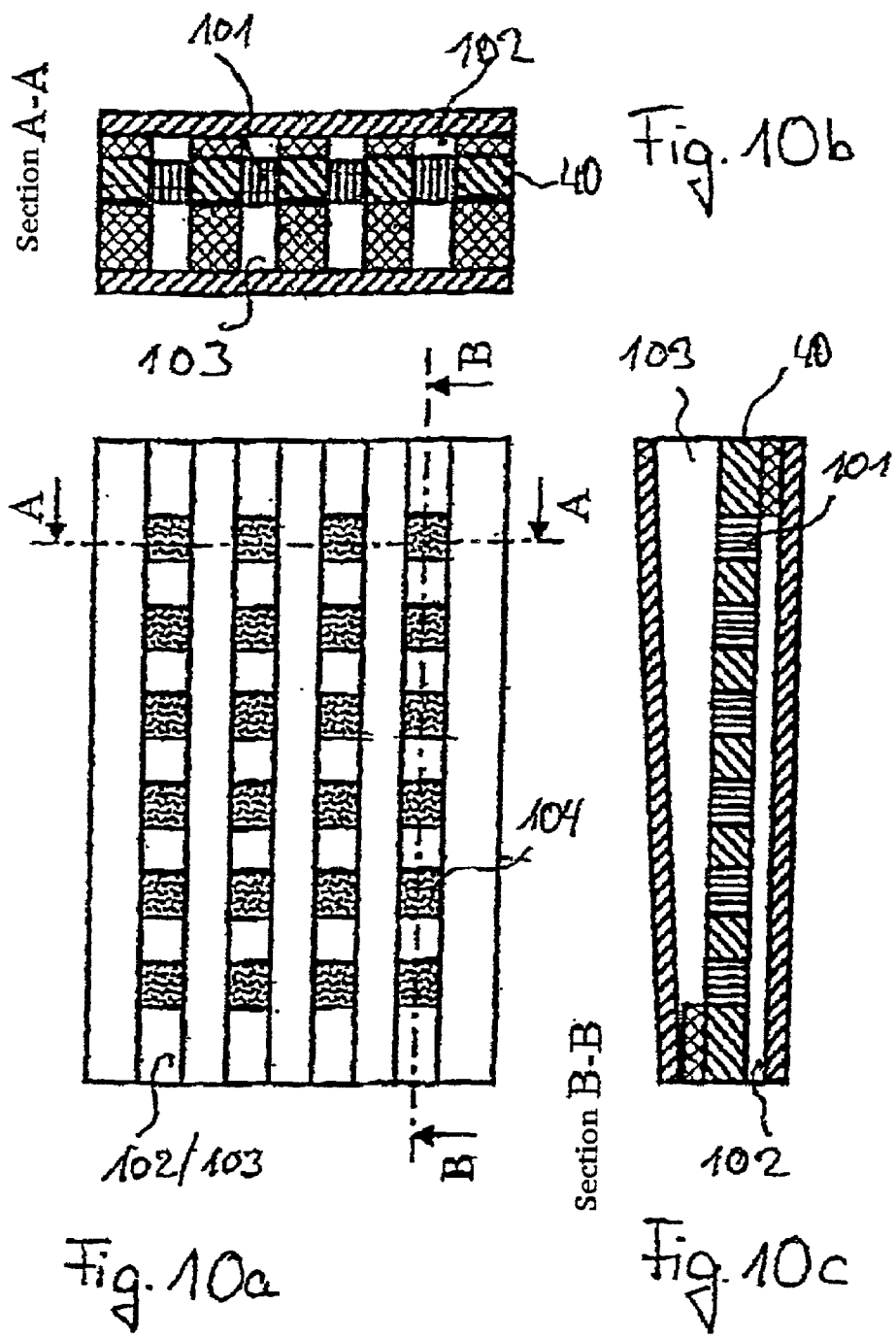
Figure 11:
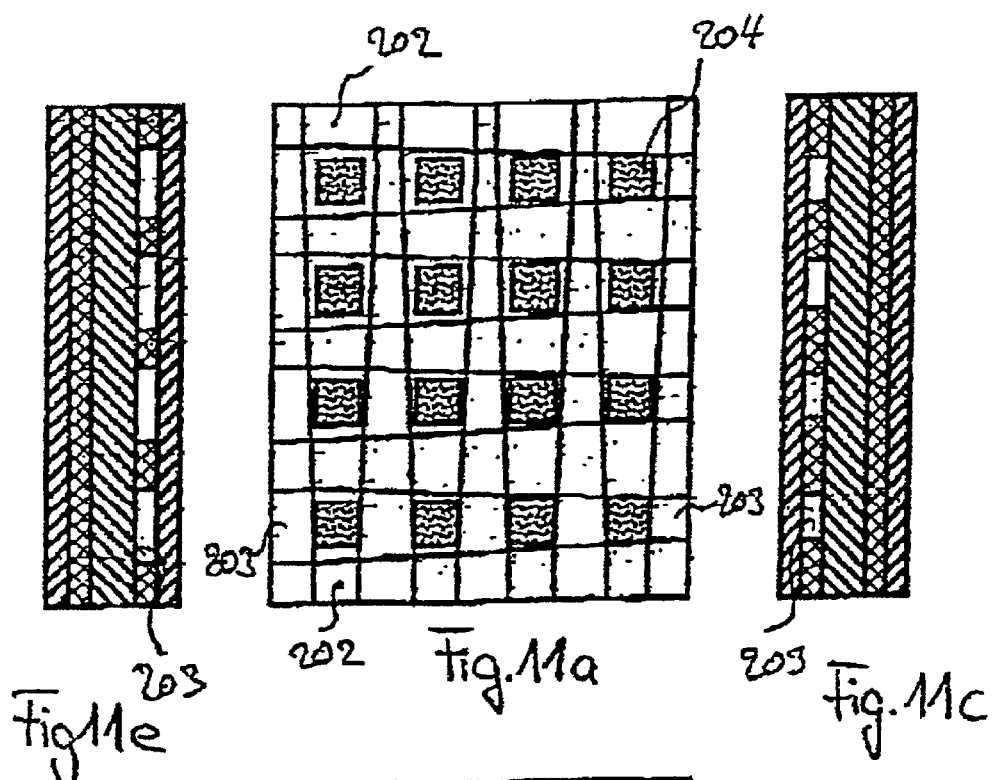

FIGS. 10a, 10b and 10c show an illustration analogous to FIGS. 3a, 3b and 3c, with the feed channels 102 and the discharge channels 103 altering their height and thus influencing the flow. Due to the thickness of the central structural layer 40, the reaction areas 104 and the reaction channels 101 have a uniform length.

FIGS. 11a, 11b, 11c, 11d and 11e show a three-dimensional cruciform structure of the flow in an illustration analogous to FIGS. 4a, 4b, 4c, 4d and 4e and 5a, 5b and 5c, with altered cross sections of the feed channels 202 and discharge channels 203 to specifically influence the flow. The size of the reaction channels in the reaction areas 204 is unchanged here.

Figure 12:
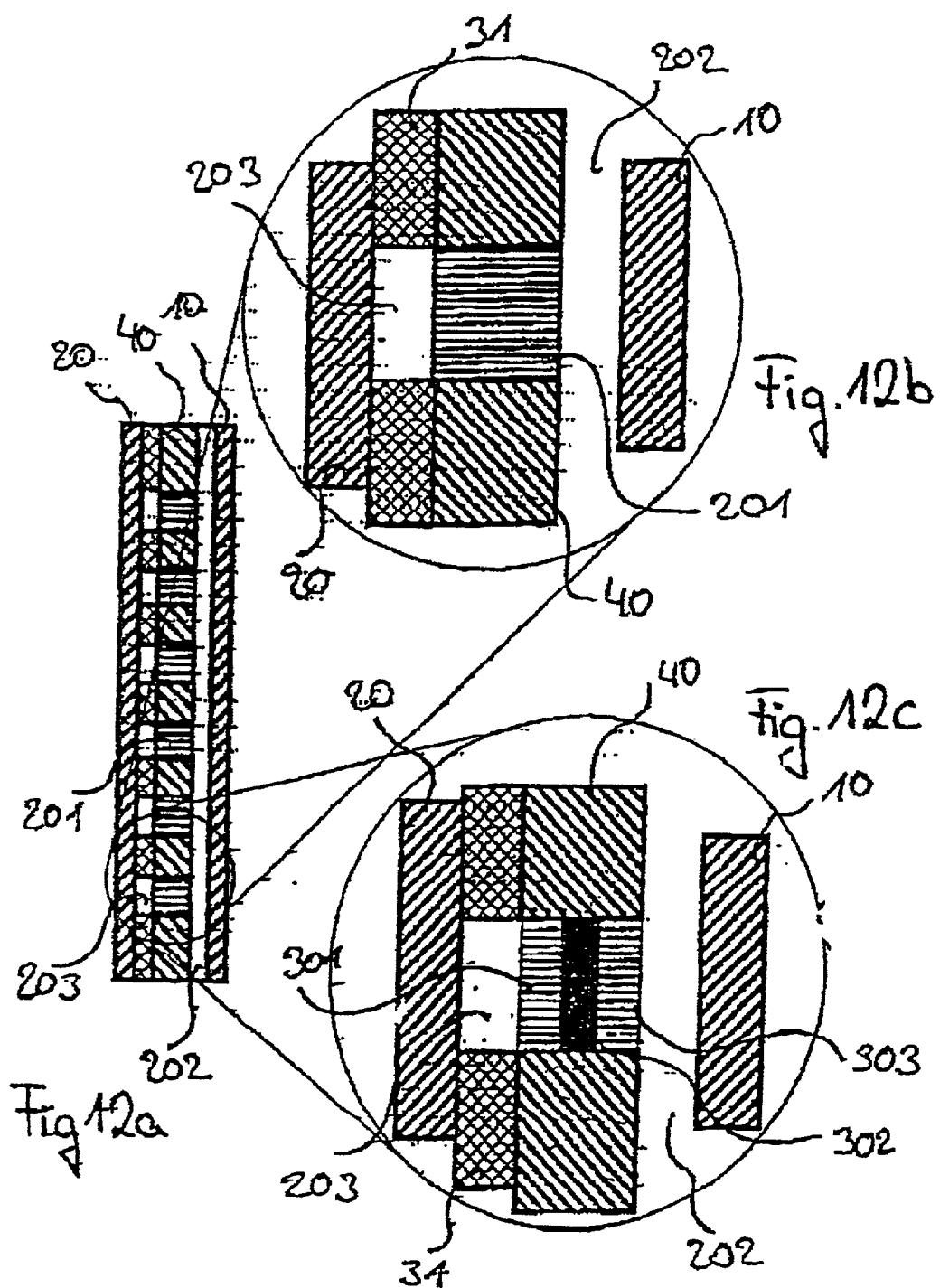

FIG. 12a shows the illustration of FIG. 5c of the cruciform structure with two detail variants 12b and 12c. The detail 12b illustrates the structure composed of the cover layers 10 and 20 and a central layer 40 having the reaction areas in the reaction channels 201 and the feed channels 202 and the discharge channels 203. In detail 12c the reaction channels 201 of the variant 12b are replaced in each case by a three-layer microstructure. Said microstructure comprises two layers 301 and 303 for smoothing and stabilizing the feed flow and discharge flow 202 and 203 and also an actual reaction layer 302 made of further microchannels and, for example, a glass fleece.

Figure 13:
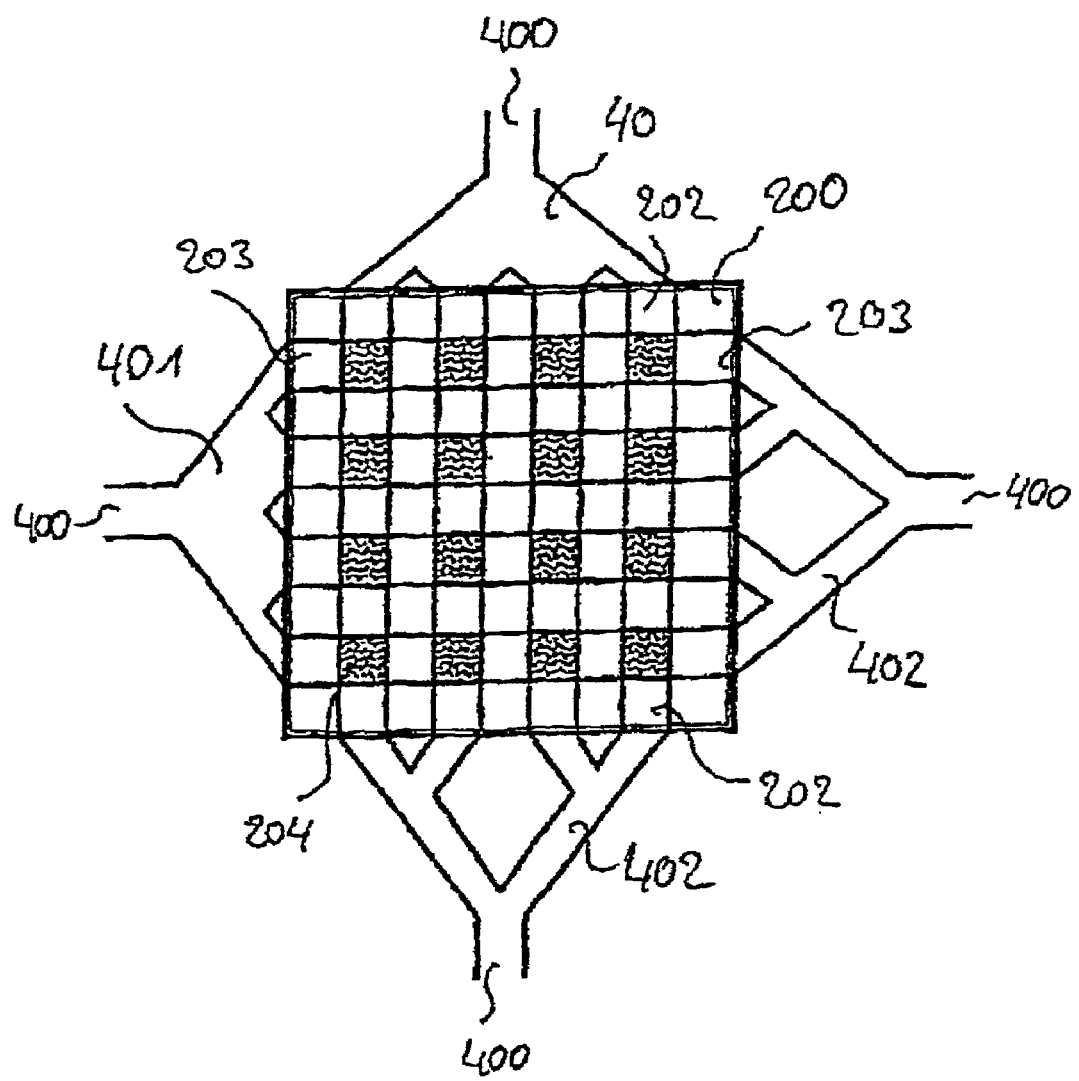

FIG. 13 shows a connection variant of the microcruciform structure 200 according to FIGS. 4a, 4b, 4c, 4d, 4e and 5a, 5b and 5c with two microflow channel variants 401 and 402. Both variants connect a channel for the fluid supply 400 in each case with all parallel channels 202 and 203 of the two levels. Thus it is possible to rinse all reaction areas 204 with fluid on various feed and discharge variants at the same time.

Figure 14:
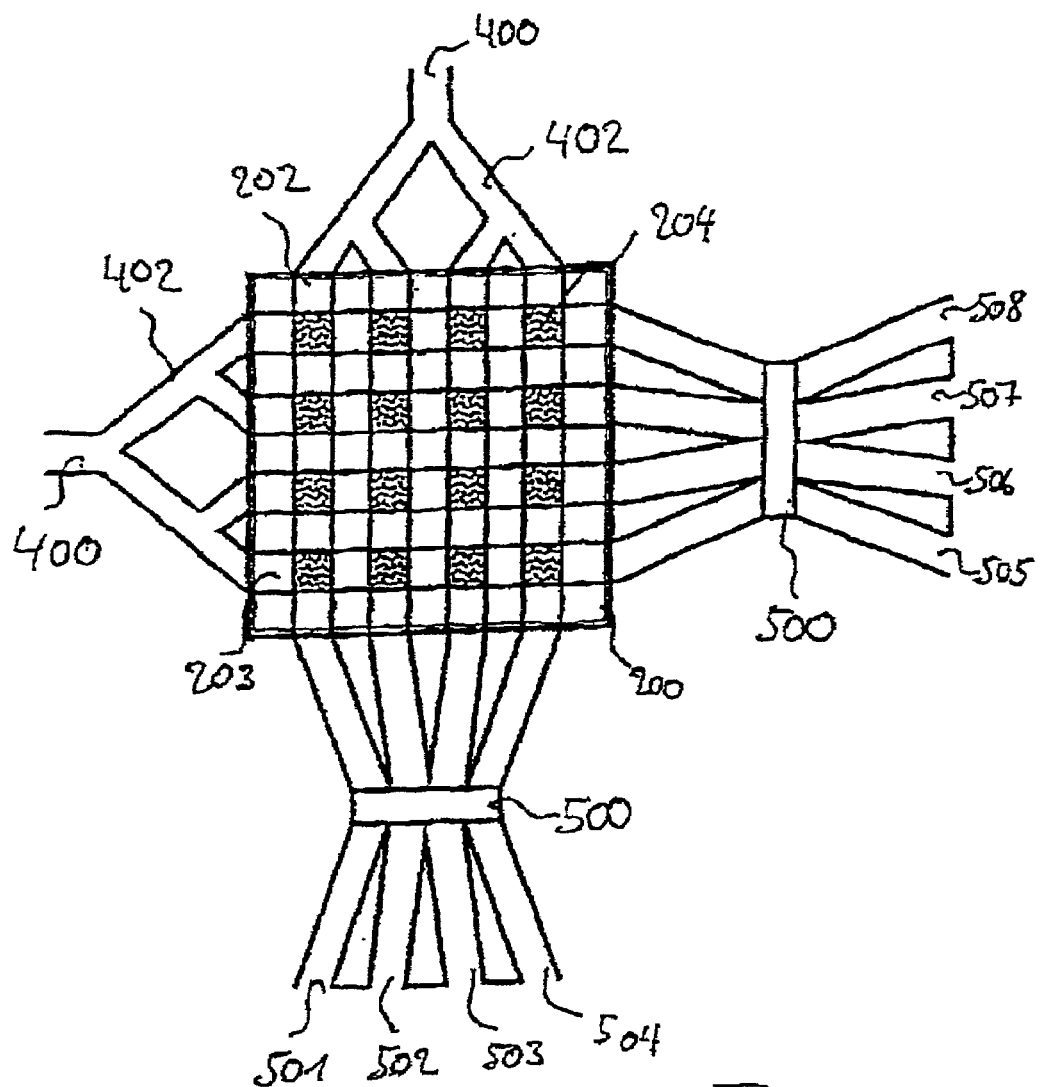

FIG. 14 shows an illustration analogous to FIG. 13 with two valves 500 integrated into the fluid supply. Said valves supply the microchannel structure 200 via the channels in the first level 202 and the second level 203. This makes it possible to rinse the reaction channels in the reaction areas 204 with fluid. It is possible to rinse one, more or all reaction areas 204 with fluid at the same time. The valve position and the direction of flow through the reaction channels make it possible to rapidly realize any fluid supply cycles. All that is required here is to change the position of the valves 500 and to apply superatmospheric or subatmospheric pressure. The uniform feeds 400, here with the channel variant 402, may also be integrated into the fluid cycles.

FIG. 15a shows a design variant of the valve 500 of FIG. 14 with further sectional illustrations 15b and 15c. The valve is designed horizontally in microtechnique. It consists essentially of a disk 509 and a plate 600. The plate is linked to the microstructure 200 via channels 601 to 604 so that optionally the fluids of the feed channels or of the microtanks behind the channels 501 to 504 can be pumped into the channels 202 of the microstructure. The assignment can be altered in series by turning the valve disk 509. According to FIG. 14, said valve 500 can also be connected to both channel structures 202 and 203 of the cruciform structure 200. This makes it possible to wet the reaction channels individually with fluid. In analogy to the rigid junctions 401 and 402 of FIG. 13, the individual microchannels 601 to 604 are optionally connected via a central feed 510 in the valve 500, for example for uniform rinsing during purification or other uniform steps, for example during the location-resolved synthesis in the reaction support.

Figure 16B:
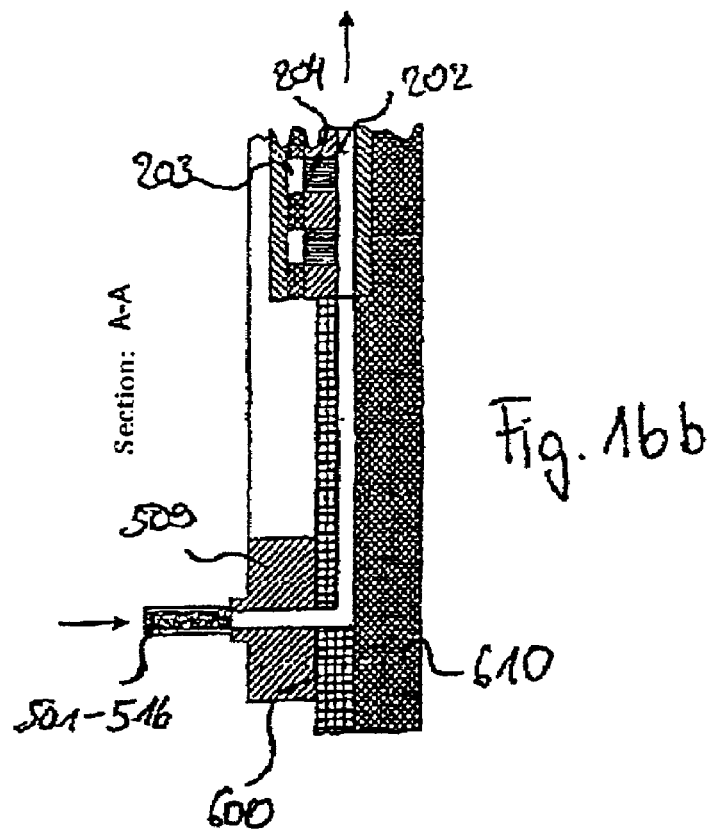
Figure 16A:
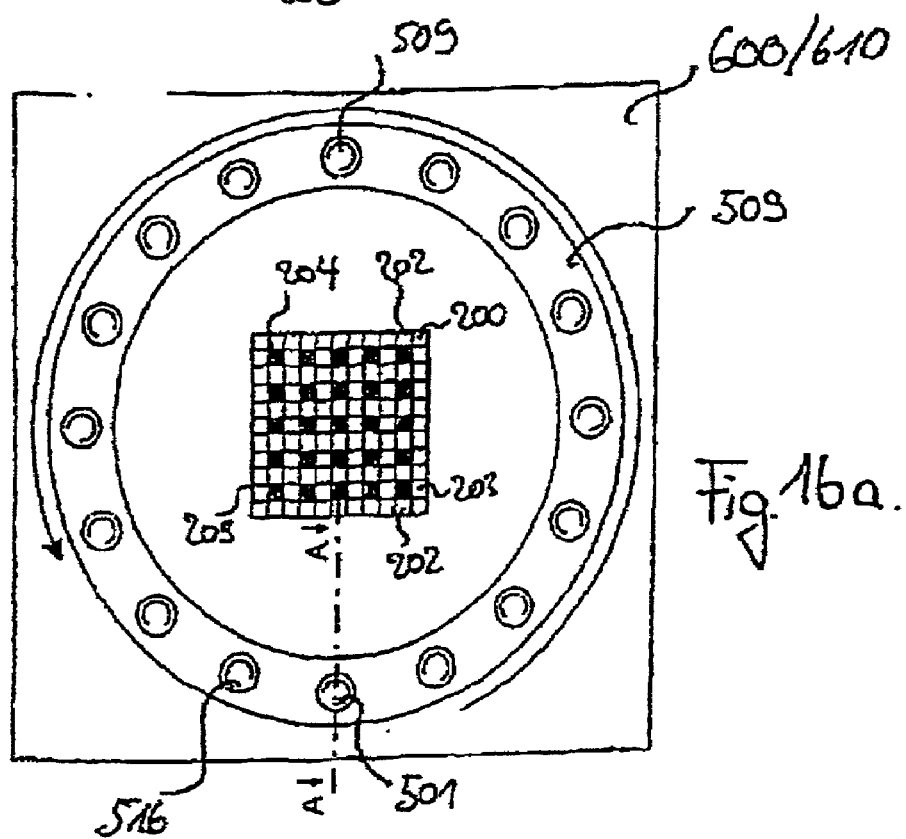

FIG. 16a shows another design variant of the multiplex valve 500 with the sectional illustration 16b.

Here, the individual supply channels 501 to 516 are arranged in a circle around the reaction support 200. The principle corresponds to FIGS. 15a, 15b, 15c. However, said design variant makes it possible to realize more or bigger connections. The disk 509 is again located on a two-layer base plate 600 and 610.

Figure 17:
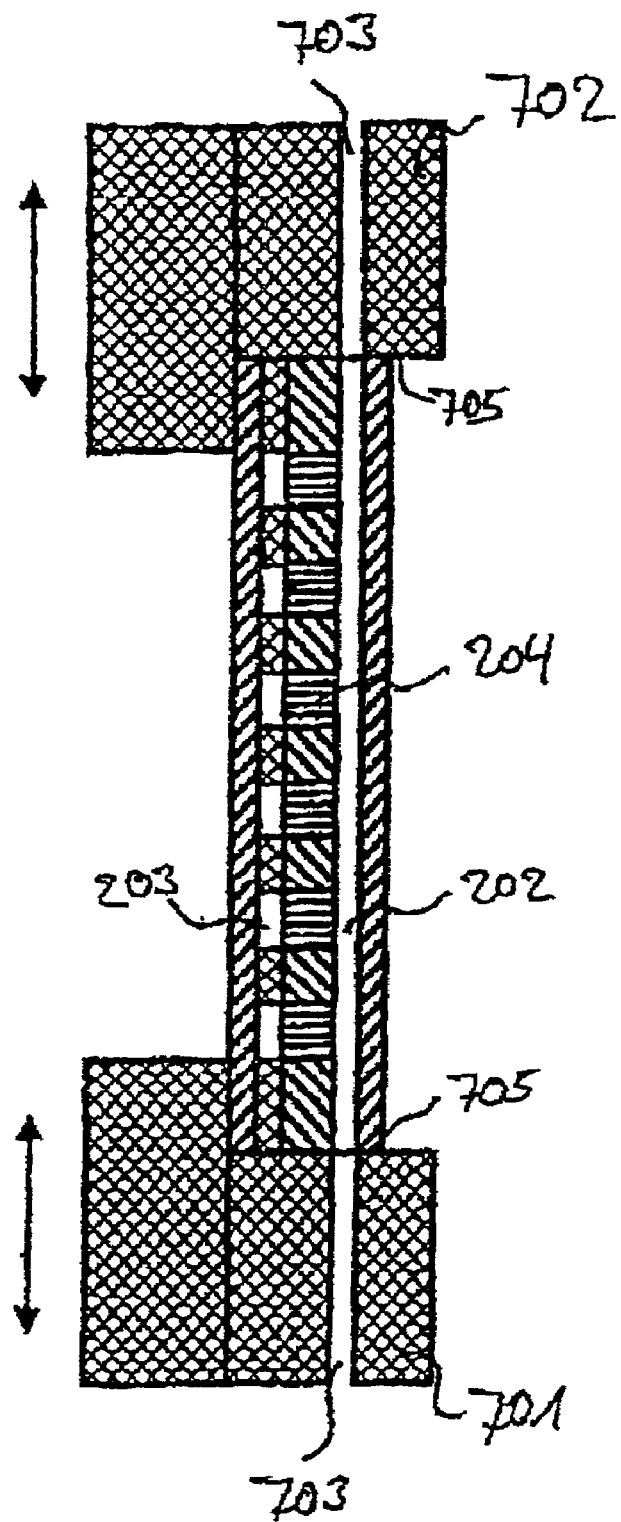

FIG. 17 shows a cross section of a fluidic reaction support which is held by a clamping device which is provided with two opposite clamping jaws 701 and 702 with an integrated flow guide 703, and said flow guide in a single flow level 202 requires no bend, etc. in the channels. The same arrangement is also possible for the channels 203. Furthermore illustrated is a narrow sealing area 705.

Figures 18, 19:
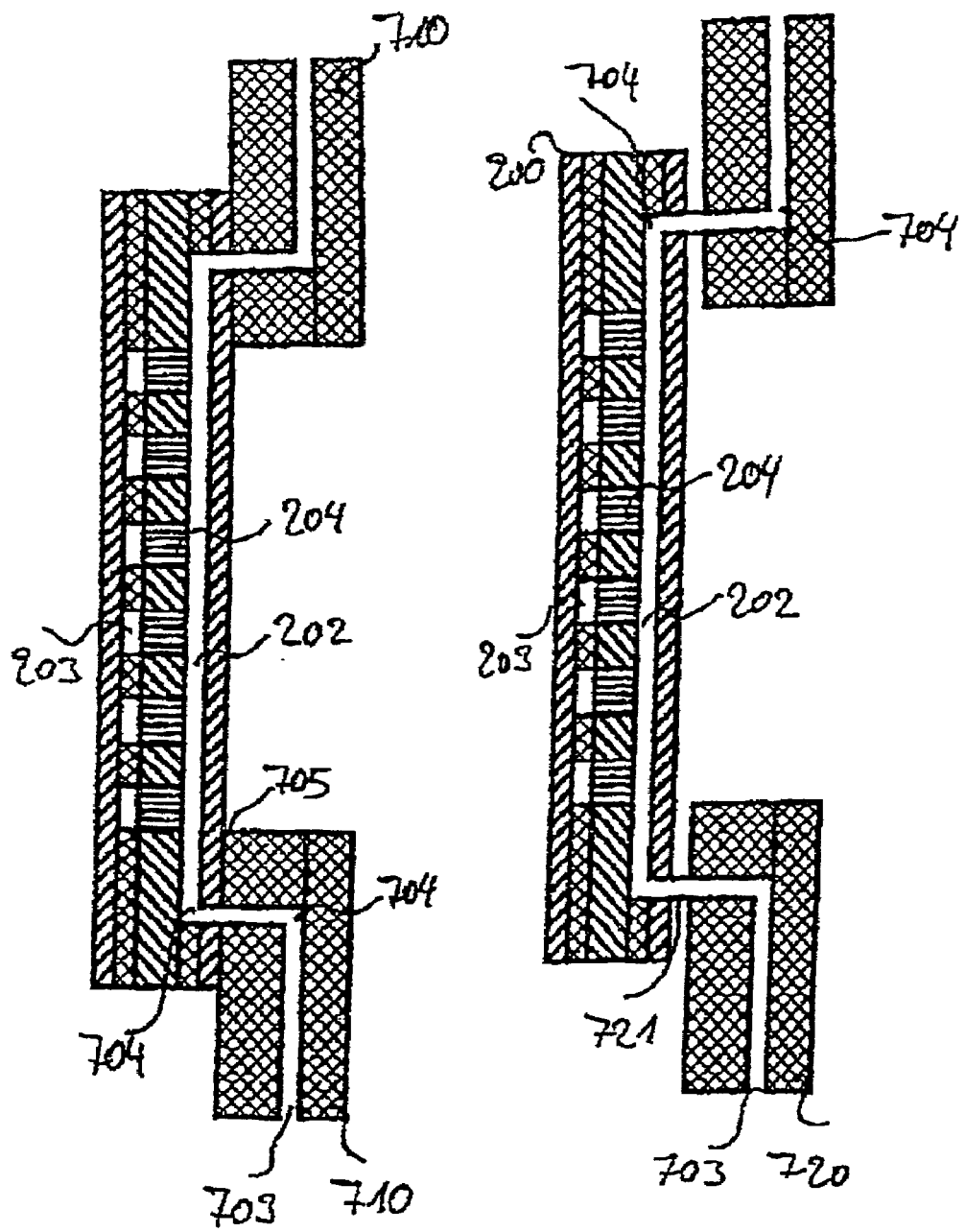

FIG. 18 shows another connection variant with flow guide 703 with bends 704 in at least two levels. Furthermore illustrated is a broad sealing area 705 in the support 710.

FIG. 19 shows another connection variant with flow guides 703 with bends 704 in at least two levels. Microlegs 721, analogous to a semiconductor technology processor, connect the base 720 with the reaction support 200 and the channels 202. The channels 203 can be connected analogously. A sealing is carried out through the microlegs 721 by adhesive bonding or plugging-in.

Figure 20:
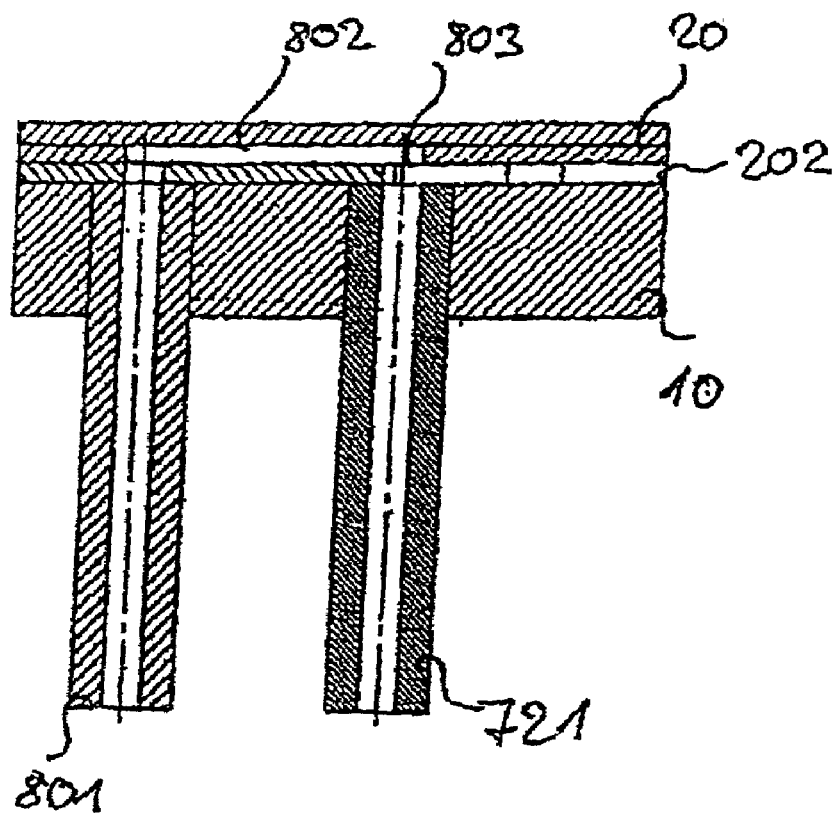

FIG. 20 shows, on the basis of the example of the microlegs 721 of FIG. 19, an after-rinse 803 for avoiding deposits in a bend of the flow and the risk of a delay connected therewith. Said microlegs 721 are anchored in the lower cover layer 10 in the reaction support. The second row of purification legs 801 makes it possible to specifically rinse the channels 802 in the corners 803 with fluid and thereby avoid or remove a deposit.

The invention claimed is:

1. A microfluidic reaction support comprising a flow channel structure for directing fluids for the synthesis of oligomers or polymers, said flow channel structure comprising:
   fluid feed channels for feeding fluid to reaction areas, each of said fluid feed channels having a non-uniform cross-section for influencing the flow of said fluid;
   fluid discharge channels for discharging fluid from the reaction areas, each of said fluid discharge channels having a non-uniform cross-section for influencing the flow of said fluid; and
   reaction areas formed by connecting channels which connect the fluid feed channels with fluid discharge channels, said connecting channels being arranged in a side-by-side relationship and at an obtuse angle to said fluid feed channels and to said fluid discharge channels measured in a direction of fluid flow such that fluid can be discharged from each reaction area with circumvention of the particular other reaction areas (4; 104).

2. The microfluidic reaction support as claimed in claim 1,
   wherein each of said fluid feed channels has a tapered cross-section from an input and to a discharge end, and each of said fluid discharge channels is tapered from an input end to a discharge end.

3. The microfluidic reaction support as claimed in claim 1, wherein each of said connecting channels has a non-uniform cross-section for influencing fluid flow.

4. The microfluidic reaction support as claimed in claim 1, wherein the fluid feed channels run essentially parallel to one another and are disposed in a first level of the microfluidic reaction support, the fluid discharge channels are disposed in a second level of the microfluidic reaction support, and the connecting channels with the reaction areas (104) are located perpendicular or nearly perpendicular to said levels.

5. The microfluidic reaction support as claimed in claim 4, wherein the fluid feed channels cross the fluid discharge channels at an angle in a projection perpendicular to the first and second level.

6. The microfluidic reaction support as claimed in claim 1, further comprising a valve system for individually charging or discharging each flow channel.

7. The microfluidic reaction support as claimed in claim 1, wherein the flow channel structure is provided on one side or on both sides with a transparent cover layer.

8. The microfluidic reaction support as claimed in claim 7, wherein the flow channel structure is provided on both sides with a transparent cover layer, in which the transparent cover layers comprises a glass or plastic and a structure of microlenses is integrated into said cover layers such that the incident light is focused on the reaction areas and the reflected light of a detection reaction is concentrated accordingly.

9. The microfluidic reaction support as claimed in claim 7, in which the transparent cover layers comprises a multiplicity of parallel fused glass fibers which form a transparent honeycomb structure such that the incident light and the reflected light are parallelized and the light is prevented from spreading sideways, due to reflection, in the cover layer.

10. The microfluidic reaction support as claimed in claim 1, wherein the walls between the feed channels and the discharge channels comprise lightproof material.

11. The microfluidic reaction support as claimed in claim 4, wherein the connecting channels (104; 204) comprise a plurality of glass fiber bundles fused together from which the glass fiber cores have been etched out to form microchannels.

12. The microfluidic reaction support as claimed in claim 11, wherein plurality of glass fiber bundles is arranged in the area of the reaction area.

13. The microfluidic reaction support as claimed in claim 4, wherein the first and second levels of the microfluidic reaction support each comprise a silicon layer into which a multiplicity of small channels has been etched.

14. The microfluidic reaction support as claimed in claim 4, wherein a plurality of levels with flow channels are arranged on top of one another such that the reaction areas in the projection perpendicular to the flow levels are not superimposed and can be photoactivated individually by light and light can be detected, likewise location-specifically, for each of the reaction areas.

15. The microfluidic reaction support as claimed in claim 1, further comprising an integrated programmable light source matrix.

16. The microfluidic reaction support as claimed in claim 1, further comprising an integrated detection unit in the form of a CCD matrix integrated.

17. The microfluidic reaction support as claimed in claim 1, wherein a plurality of in different receptors is each bound to selected areas in the support.

18. The microfluidic reaction support as claimed in claim 17, wherein the receptors are selected from the group consisting of nucleic acids and nucleic acid analogs.

19. The microfluidic reaction support as claimed in claim 17, wherein the receptors are synthesized on the support from individual synthesis building blocks.

20. The microfluidic reaction support as claimed in claim 17, wherein a building block is provided between receptor and support, which allows the receptor to be removed by cleavage.

21. A method of using a microfluidic reaction support, comprising steps of:
providing the microfluidic reaction support as claimed in claim 1;
performing synthesis of oligomers or polymers with said microfluidic reaction support.

22. The method as recited in claim 21, wherein said performing step comprises wet-chemical synthesis of oligomeric or polymeric probes from a list consisting of DNA, RNA, PNA, and LNA.

23. The method as recited in claim 21, wherein said performing step comprises integrated synthesis and analysis of polymers.

24. The method as recited in claim 21, wherein said performing step comprises optical analysis of hybridization of synthesized polymeric probes with complementary fragments.

25. The method as recited in claim 21, wherein said performing step comprises efficient highly parallel combined wet-chemical and light-controlled synthesis of oligomeric or polymeric probes; and
subsequent optical analysis of the hybridization with complementary fragments.

26. The method as recited in claim 21, wherein said performing step comprises light-controlled synthesis of oligomeric or polymeric probes; and
subsequent optical analysis of the hybridization with complementary fragments.

27. A method of using a microfluidic reaction support, comprising steps of:
providing the microfluidic reaction support as claimed in claim 7; and
measuring luminescence and fluorescence through the transparent cover layer in a backlight process.

28. A method of using a microfluidic reaction support, comprising steps of:
providing the microfluidic reaction support as claimed in claim 7;
exposing each reaction area to light of a defined wavelength via a programmable light source matrix, wherein each reaction is biochemically functionalized via the light and the supply of fluid; and
optically monitoring all processes in the reaction support simultaneously via the second transparent cover layer.

29. A method of using a microfluidic reaction support, comprising steps of:
providing the microfluidic reaction support as claimed in claim 7; and
measuring luminescence, fluorescence and absorption through the two transparent cover layers in a transmitted-light process.

* * * * *